United States Patent [19]
Bourne et al.

[11] Patent Number: 6,083,205
[45] Date of Patent: *Jul. 4, 2000

[54] MULTIPLE VALVE SINGLE PORT MANIFOLD

[75] Inventors: Thomas Michael Bourne, Mountain View; Anant Hegde, Newark; Harm TenHoff, Mountain View, all of Calif.

[73] Assignee: Intella Interventional Systems, Sunnyvale, Calif.

[*] Notice: This patent is subject to a terminal disclaimer.

[21] Appl. No.: 09/014,532

[22] Filed: Jan. 28, 1998

[51] Int. Cl.[7] .................................................. A61M 5/00
[52] U.S. Cl. .......................... 604/246; 604/248; 604/249; 604/537; 604/99; 137/883
[58] Field of Search ................................ 604/30, 32, 33, 604/96, 99, 246, 248, 249, 256, 537; 606/108, 198; 137/883

[56] References Cited

U.S. PATENT DOCUMENTS

| | | |
|---|---|---|
| 4,838,269 | 6/1989 | Robinson et al. ...................... 128/344 |
| 4,950,255 | 8/1990 | Brown et al. ............................ 604/250 |
| 5,197,948 | 3/1993 | Ghodsian ................................... 604/27 |
| 5,226,889 | 7/1993 | Sheiban .................................... 604/101 |
| 5,242,387 | 9/1993 | Loughlin .................................... 604/43 |
| 5,288,290 | 2/1994 | Brody . | |
| 5,423,744 | 6/1995 | Gencheff et al. . | |
| 5,423,769 | 6/1995 | Jonkman et al. . | |
| 5,447,494 | 9/1995 | Dorsey, III ................................. 604/43 |
| 5,562,614 | 10/1996 | O'Donnell ................................. 604/65 |
| 5,725,535 | 3/1998 | Hegde et al. ............................ 606/108 |
| 5,788,708 | 8/1998 | Hegde et al. ............................. 604/96 |

FOREIGN PATENT DOCUMENTS 0 345 396 A1   12/1988   European Pat. Off. ......... A61M 5/14

*Primary Examiner*—Ronald K. Stright, Jr.
*Assistant Examiner*—Jeremy Thissell
*Attorney, Agent, or Firm*—Limbach & Limbach LLP

[57] ABSTRACT

The present invention relates to a multiple valve single port manifold for use with a multiple lumen catheter. The inventive manifolds comprise a conduit with an entry port; a plurality of means for connecting the conduit to a plurality of catheter lumens, such that each lumen is capable of being in fluid communication with the entry port; and a plurality of means for controlling access from the conduit to the plurality of catheter lumens, such that each controlling means independently regulates access from the conduit to its corresponding catheter lumen. Because each catheter lumen is independently accessible from the same manifold port, the inventive devices are useful in any medical context where a need exists to independently control access to spatially proximal sites within a patient's passageway. For example, practice of the present invention allows a fluid to be delivered to any combination of spatially proximal vessel sites, or more typically, allows multiple balloons mounted on a catheter to be independently inflated and/or deflated during angioplasty procedures.

25 Claims, 10 Drawing Sheets

MULTIPLE VALVE SINGLE PORT MANIFOLD

BACKGROUND

The present invention generally relates to devices for use with catheters. More particularly, the present invention relates to multiple valve single port manifolds for use with multiple balloon catheters that allow any combination of balloons to be independently (and simultaneously) inflated or deflated.

Although used in a variety of medical procedures, multiple balloon catheters are most widely associated with percutaneous transluminal coronary angioplasty. The procedure typically involves advancing a balloon catheter to the partially blocked coronary artery and inflating one or more balloons at the blockage site. The inflated balloons stretch and/or fracture the blockage thereby enlarging the opening of the previously occluded vessel.

The inflation and/or deflation of the balloons is controlled by a manifold which controls access to the catheter lumens from one or more ports. A drawback to prior art designs for single port manifolds is that the individual balloons may not be separately manipulated. In other words, either all of the balloons are simultaneously inflated or deflated.

Multiple port manifolds solve this problem by providing a separate port for controlling the inflation and/or deflation of each balloon. However, the additional ports can result in a bulky device that can be difficult to manipulate by a single operator. Because catheters that are easy to use and manipulate are highly desirable, a need exists for a single port catheter manifold that allows each of the individual balloons to be independently manipulated.

SUMMARY OF THE INVENTION

The present invention relates to a multiple valve single port manifold for use with a multiple lumen catheter. Because each catheter lumen is independently accessible from the same manifold port, the inventive devices are useful in any medical context where a need exists to independently control access to target sites within a patient's passageway. For example, practice of the present invention allows fluid to be delivered to any combination of spatially distributed vessel sites, or more typically, allows multiple balloons mounted on a catheter to be independently inflated and/or deflated.

The inventive manifolds comprise (1) a conduit with an entry port; (2) a plurality of means for connecting the conduit to a plurality of catheter lumens, such that each lumen is capable of being in fluid communication with the entry port; and (3) a plurality of means for controlling access from the conduit to the plurality of catheter lumens, such that each controlling means independently regulates access from the conduit to its corresponding catheter lumen. However, it is not necessary for the correspondence between the controlling means and its associated lumens be one to one. For example, a single controlling means may also control access to a plurality of corresponding lumens.

DETAILED DESCRIPTION OF THE PREFERRED EMBODIMENTS

The present invention relates to a single port manifold for use with a multiple lumen catheter such that each catheter lumen is independently accessible from the same manifold port. The inventive manifold may be used with a multiple lumen medical device in any context where access from a single entry point to any combination of target sites, such as within a blood vessel or urethra, is desirable. For example, targeted delivery of a drug or fluid to lesion sites in a stenosed blood vessel (or other body canal or channel) is possible using a multiple lumen catheter having different exit points along the catheter shaft. Another use of the present invention is with multiple balloon catheters during angioplasty procedures. Although the manifold is used similarly in both types of procedures, since angioplasty is the more prevalent medical procedure, the present invention will be described with multiple balloon catheters where context is required for the purposes of illustration.

In general, the inventive manifolds comprise (1) a conduit having an entry port; (2) an elongated shaft for containing a catheter shaft therein; and, (3) a plurality of valves disposed within the conduit wherein at least two of the valves have an opened and a closed position. Moreover, at least two of the valves also include a first channel and second channel formed therein which are positioned such that the first channel aligns with the conduit providing access through the valve when the valved is placed in the closed position, and the second channel aligns with the conduit providing access through the valve as well as fluidly coupling the conduit to the elongated shaft when the valve is placed in the opened position.

Figure 1A:
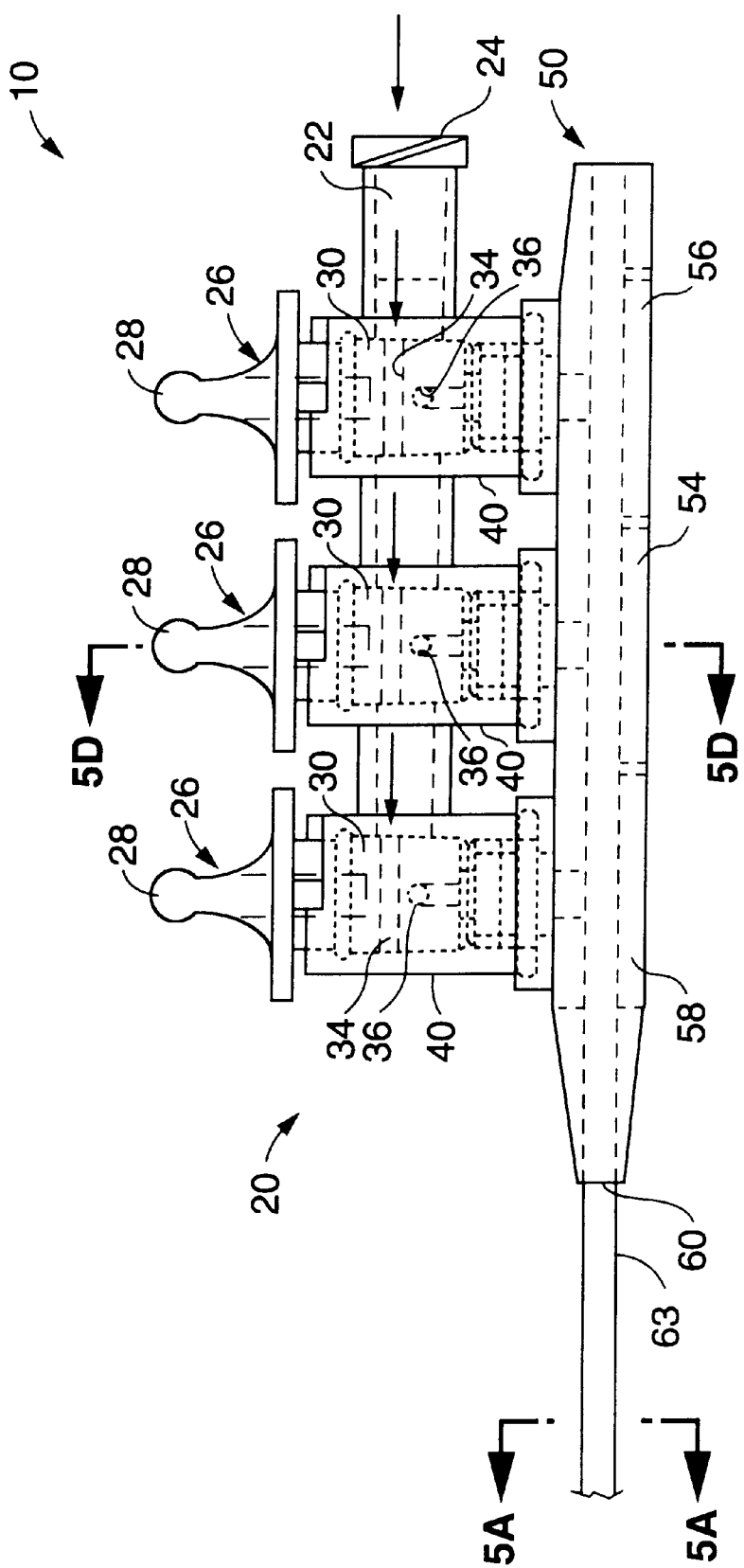
FIG. 1A is a side view of the preferred embodiment wherein all of the valve gates are in a closed position.
Figure 1B:
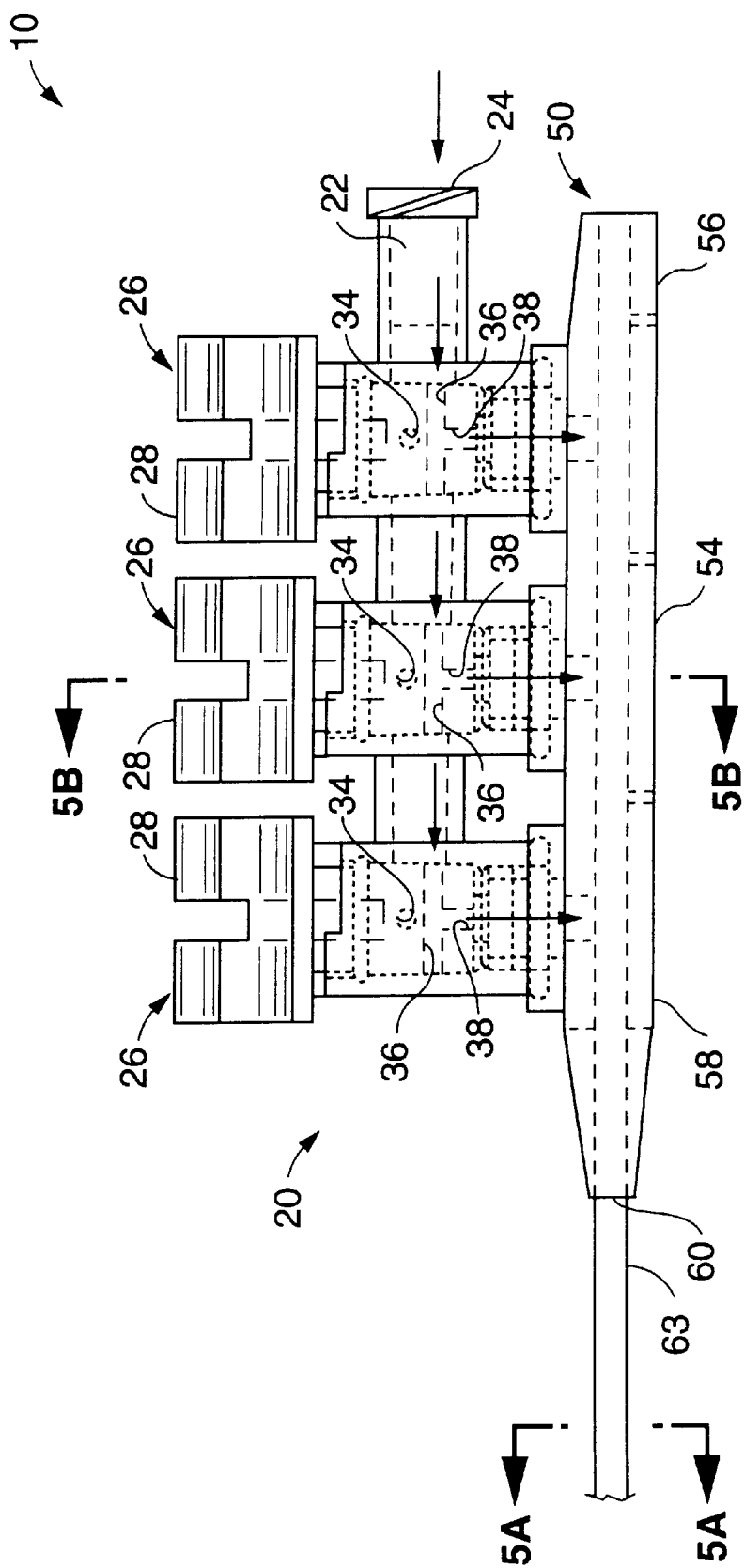
FIG. 1B is a side view of the preferred embodiment wherein all of the valve gates are in an opened position.

FIGS. 1A and 1B illustrates a preferred embodiment of the inventive manifold that has been attached to a multiple lumen catheter. Although the three valve manifold for use with a catheter having three accessible lumens will be used for the purposes of describing the invention, it is to be understood that the invention may be readily adapted for use with a catheter having two or more accessible lumens.

FIG. 1A shows the three valves of the manifold all in a closed position and FIG. 1B shows the three valves of the manifold in an opened position. Manifold 10 may be described as two constituent parts: (1) a valve assembly 20 comprising conduit 22 with entry port 24 and a plurality of valve gates 26 and valve housings 40 and (2) and an attachment assembly 50 which allows conduit 22 to be in fluid communication with each of the three catheter lumens (not pictured).

The inventive manifolds may be made of any suitable material known in the art. In preferred embodiments, rigid materials, such as polycarbonate and styrene, that are not easily compressible are preferred for forming the conduit 22, valve housings 40, and attachment assembly 50. Since some compressibility is desired for forming a tight seal between valve gates 26 and valve housings 40, slightly less rigid materials, such as polyethylene and polypropylene, are preferred for making the valve gates 26.

FIG. 2 further illustrates value assembly 20. FIG. 2A is a side view and FIG. 2B is a top view of valve assembly 20 wherein all of the valve gates 26 are in a closed position. FIG. 2C is a side view and FIG. 2D is a top view of valve assembly 20 wherein all of the valve gates 26 are in an opened position.

Valve assembly 20 is comprised of conduit 22 and a plurality of valve gates 26 with a corresponding valve housing 40 for each valve gate 26. Conduit 22 is comprised of entry port 24 at one end and is serially coupled to the each individual valve housing 40. The most distal valve housing 40 from entry port 24 forms the second end of conduit 22.

Although entry port 24 is shown to be contiguous with one end of conduit 22, entry port 24 may be placed at any point along the side of conduit 22. However, for compactness of the overall apparatus, placing entry port 24 at one end of conduit 22 is generally preferred.

Figure 3A:
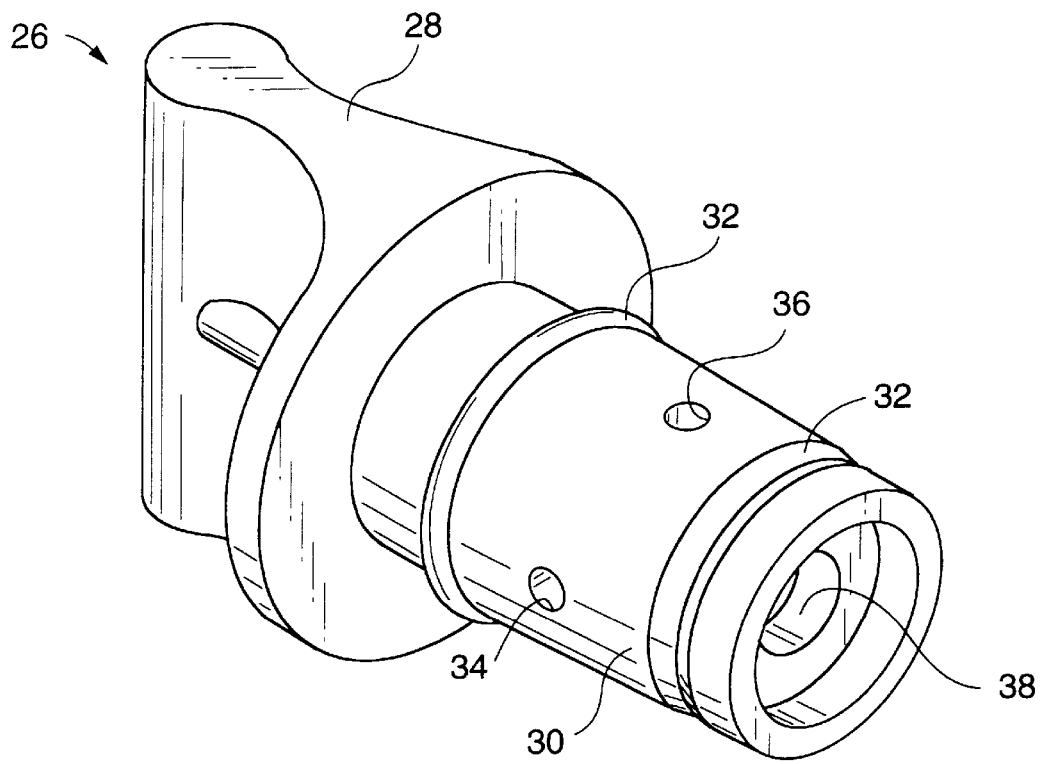
FIG. 3A is a schematic of a valve gate.
Figure 3B:
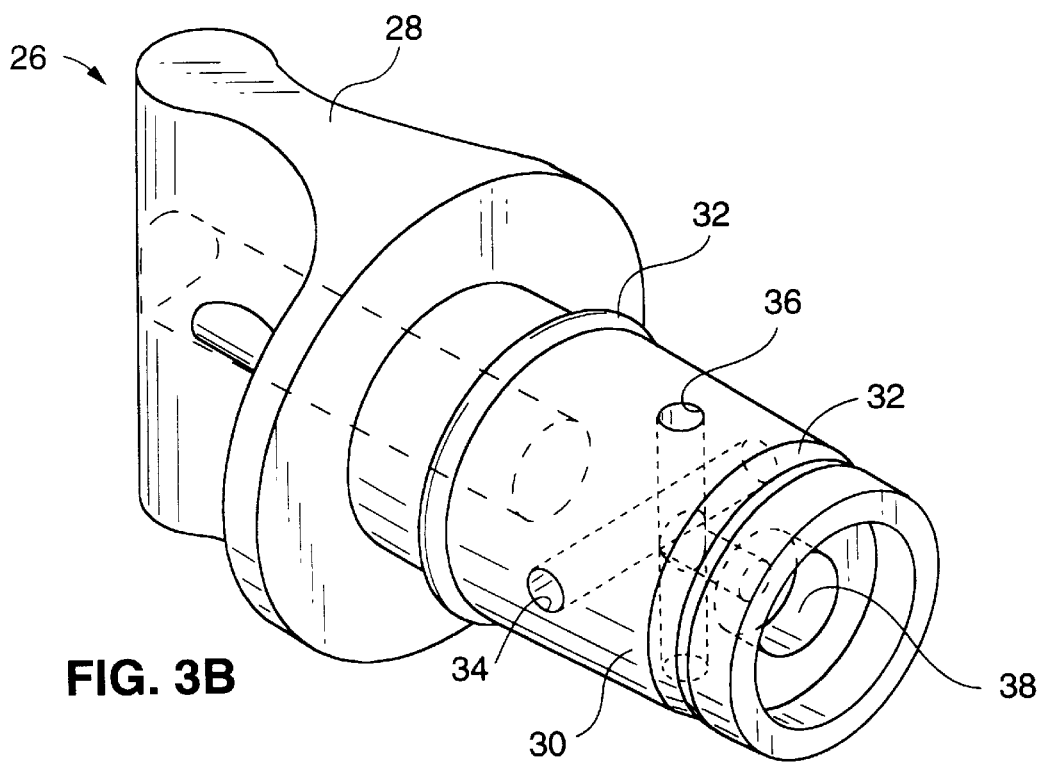
FIG. 3B is another rendition of a valve gate that details the positions with respect to each other of the two horizontal channels and the vertical channel within the valve stem.

FIGS. 3A and 3B is a detailed schematic of an individual valve gate 26 which comprises handle 28 and stem 30. Stem 30 in turn includes seals 32 at its upper and lower portions, upper horizontal channel 34, lower horizontal channel 36, and vertical channel 38. Upper horizontal channel 34 and lower horizontal channel 36 are in different horizontal planes and are placed at an angle, preferably 90°, with respect to each other. Upper horizontal channel 34 and lower horizontal channel 36 are not in fluid communication with each other. However, lower horizontal channel 36 is fluidly coupled to vertical channel 38. In preferred embodiments, connecting at 90° with respect to each other, the combination of lower horizontal channel 36 and vertical channel 38 forms a T-shaped passageway.

As it will be further described below, this unique valve gate design allows the valve gates to be part of a single common passageway (conduit 22) while allowing for each of the catheter lumens to be separately and independently accessible from the common passageway via a single entry port 24. An essential feature of this design is the placement of the upper horizontal channel 34 and lower horizontal channel 36 so that both are capable of being in fluid communication with conduit 22. Either upper horizontal channel 34 or lower horizontal channel 36 (but never both simultaneously) is in fluid communication with conduit 22.

Figure 2A:
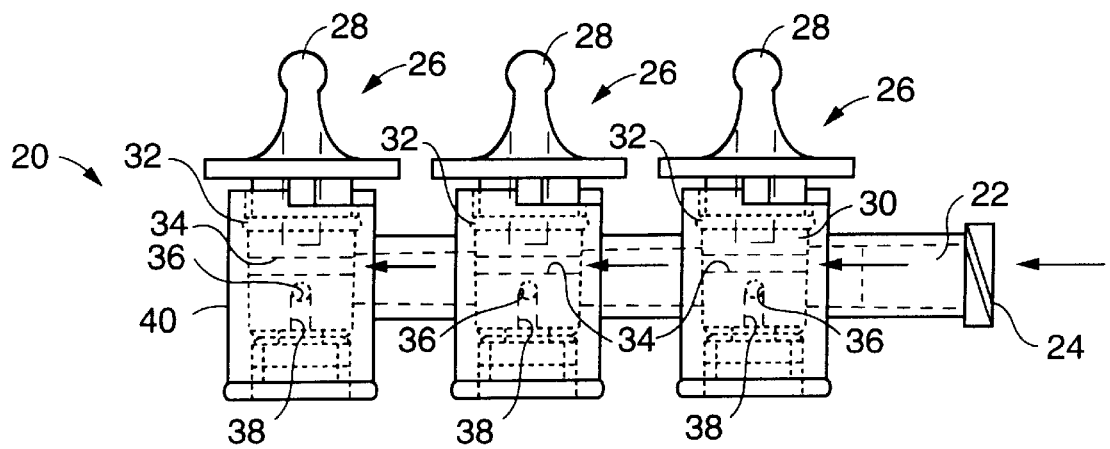
FIGS. 2A and 2B are side and top views of the preferred embodiment of the valve assembly wherein all of the valve gates are in the closed position.
Figure 2B:
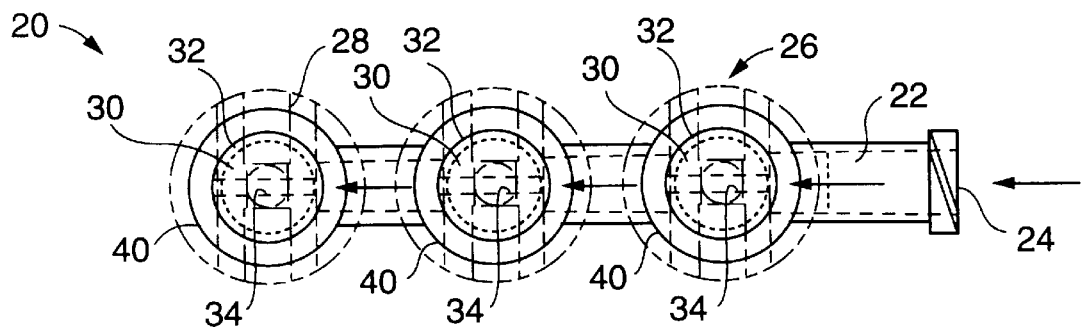

Referring to FIGS. 2A and 2B wherein all of the valve gates 26 are in a closed position, each upper horizontal channel 34 is in fluid communication with conduit 22 (as indicated by the arrows). This allows an open channel to be formed within conduit 22 through each valve gate 26 within its corresponding valve housing 40.

Figure 2C:
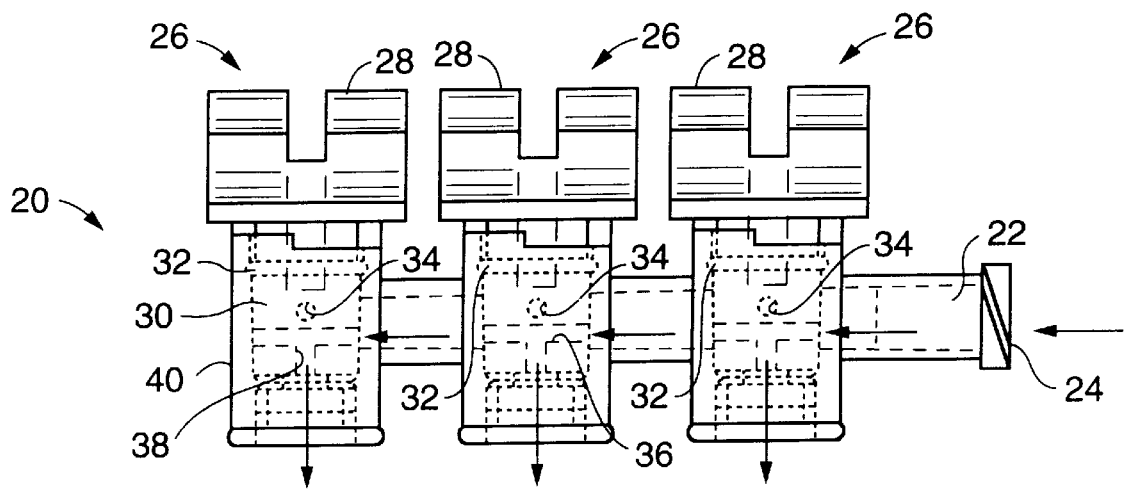
FIGS. 2C and 2D are side and top views of the preferred embodiment of the valve assembly wherein all of the valve gates are in the opened position.
Figure 2D:
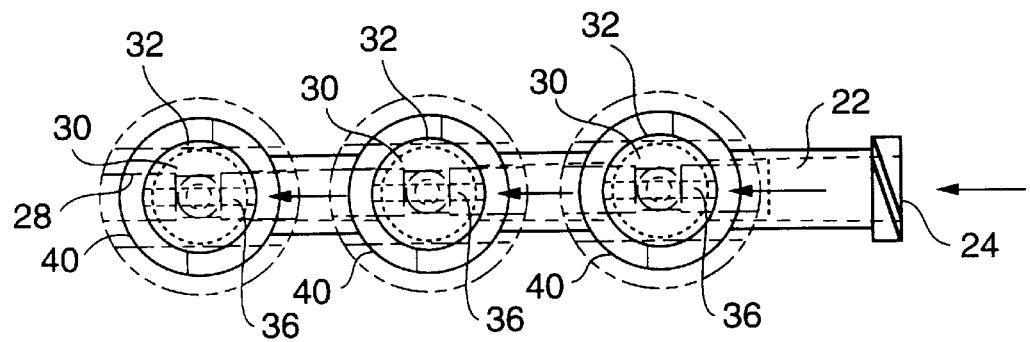

FIGS. 2C and 2D illustrate valve assembly 20 wherein all of the valves are in an opened position. As it can be seen by FIG. 2C, lower horizontal channel 36 of each valve gate 26 is in fluid communication with conduit 22 via entry port 24. In contrast to upper horizontal channel 34, lower horizontal channel 36 is also fluidly coupled to vertical channel 38. As it will be described in more detail below, vertical channel 38 of each valve gate 26 allows access from conduit 22 via entry port 24 to its associated catheter lumen.

Figure 4A:
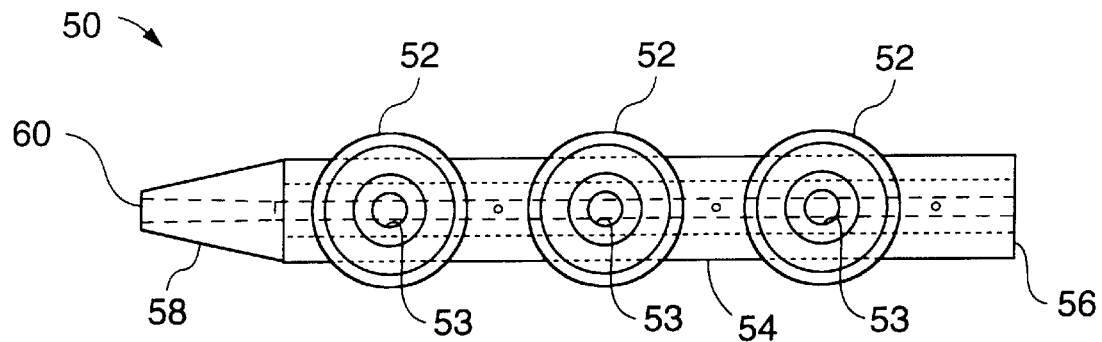
FIGS. 4A and 4B are top and side views of a preferred embodiment of the attachment assembly which connects the valve assembly of the manifold to each catheter lumen.
Figure 4B:
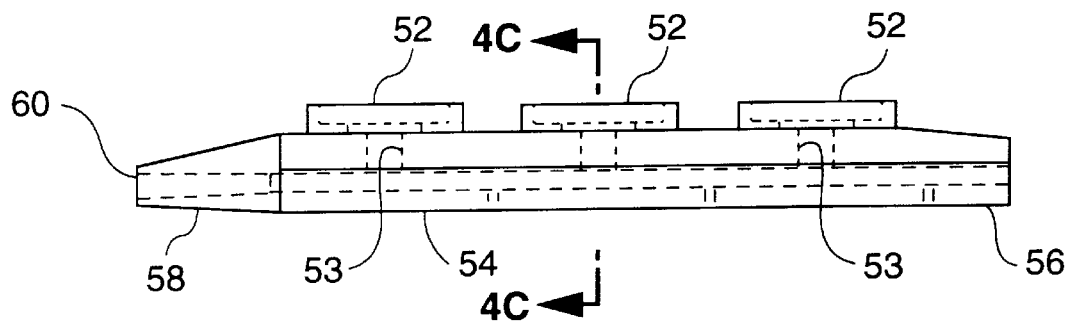

FIG. 4A is a top view and FIG. 4B is a side view of the attachment assembly of the preferred embodiment. Attachment assembly 50 comprises an elongated shaft 54 and a plurality of bases 52 to receive the corresponding plurality of valve housings 40 of valve assembly 20.

A catheter shaft (not pictured) is slidably received into elongated shaft 54 which includes a proximal end 56 and a distal end 58. An opening 60 at the most distal end 58 of elongated shaft 54 is a through-hole for the catheter shaft. Depending on the nature of the catheter being used, the most proximal end of elongated shaft 54 may be either sealed (as pictured) or may include a second opening for a guide wire port (not pictured).

Figure 4C:
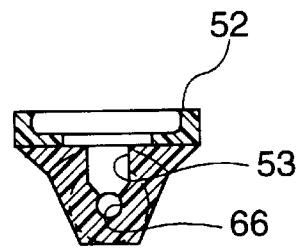
FIG. 4C is a cross section of the side view of the attachment assembly at the point indicated in FIG. 4B.

As illustrated by FIG. 4C which is a cross section of FIG. 4B, when attachment assembly 50 is connected to valve assembly 20, base channel 53 connects with vertical channel 38 and provides a passageway to its corresponding catheter lumen via catheter shaft 66. The details of this connection between base channel 53 and catheter shaft 66 will be discussed further below.

Any combination of opened and closed valve gates 26 is possible to independently control access to any combination of catheter lumens. For example, referring back to FIG. 2A, if the most distal valve gate 26 from entry port 24 were moved to an opened position, then the following would occur. Because the two proximal valve gates 26 from the entry port 24 are in the closed position, entry port 24 would be in fluid communication with the upper horizontal channels 34 of the two proximal valve gates 26 and lower horizontal channel 36 of the most distal valve gate 26. Lower horizontal channel 36 of the most distal valve gate 26 is fluidly coupled to its vertical channel 38. When valve assembly 20 is connected to attachment assembly 50, vertical channel 38 of the most distal valve gate 26 would be connected to its corresponding base channel 53 which in turn would be fluidly coupled to its corresponding catheter lumen. In the angioplasty context, only the balloon associated with the catheter lumen that is controlled by the most distal valve gate 26 would inflate and/or deflate. Other combinations of opened and closed valve gates would work similarly.

Figure 5A:
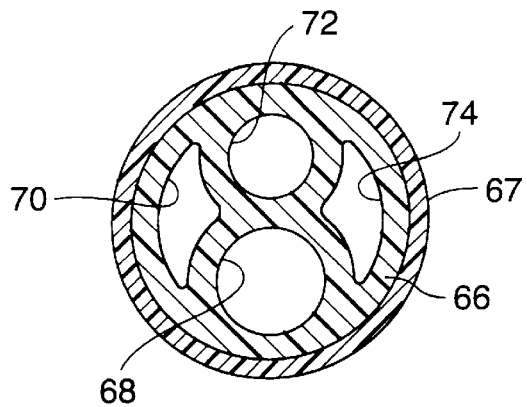
FIG. 5A is a cross section of both FIGS. 1A and 1B showing the strain relief containing the multiple lumen catheter shaft therein.

The independent access to individual catheter lumens is also illustrated by FIGS. 5A–5E. FIG. 5A is a cross section of the catheter associated with the manifold in FIGS. 1A or 1B. However, it is to be understood that the catheter depicted by FIG. 5A is for the purposes of illustration only and that the present invention may be used with any catheter where controlling access to multiple lumens is desired.

Referring to FIG. 5A, optionally contained within strain relief 67, catheter shaft 66 includes four lumens: one guide wire lumen 68 and three lumens 70, 72, and 74. As previously described, access from conduit 22 via entry port 24 to any combination of lumens 70, 72, and 74 is controlled by the positions of the corresponding valve gates 26.

Figure 5B:
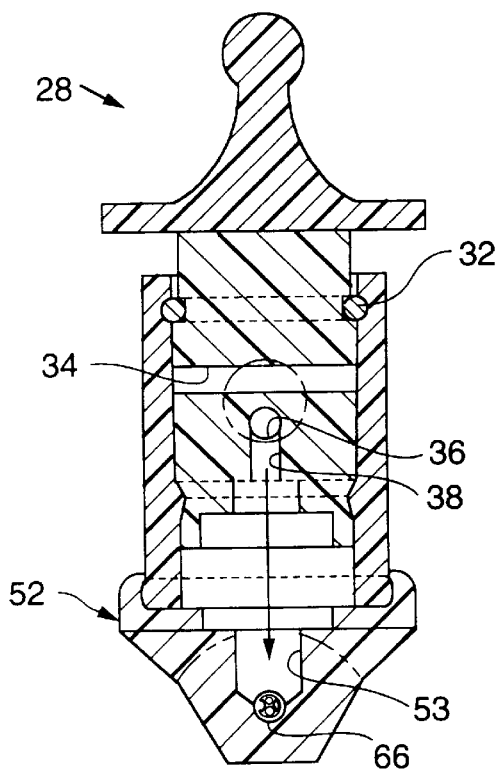
FIG. 5B is a cross section of the manifold in the closed position when coupled to a multiple lumen catheter.
Figure 5C:
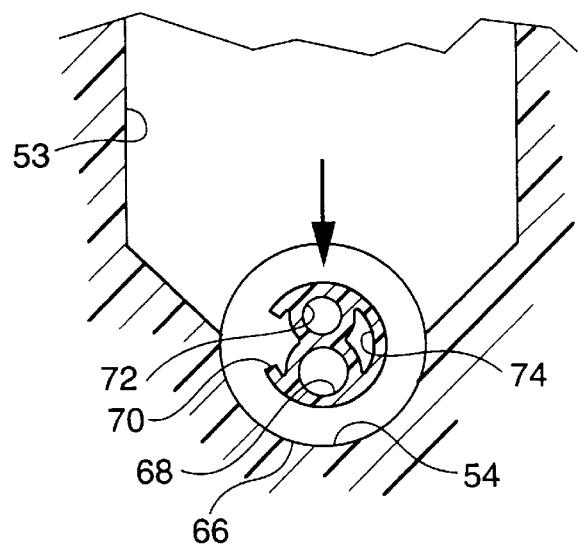
FIG. 5C is an enlarged view of the catheter shaft region of FIG. 5B.

FIG. 5B is a cross section of the manifold and catheter at the position indicated in FIG. 1A. FIG. 5C is an enlarged view of the catheter shaft region in FIG. 5B. Because valve gate 26 in the cross section is in the closed position, no communication is provided between conduit 22 (not pictured) and vertical channel 38 (and thus catheter shaft 66).

Figure 5D:
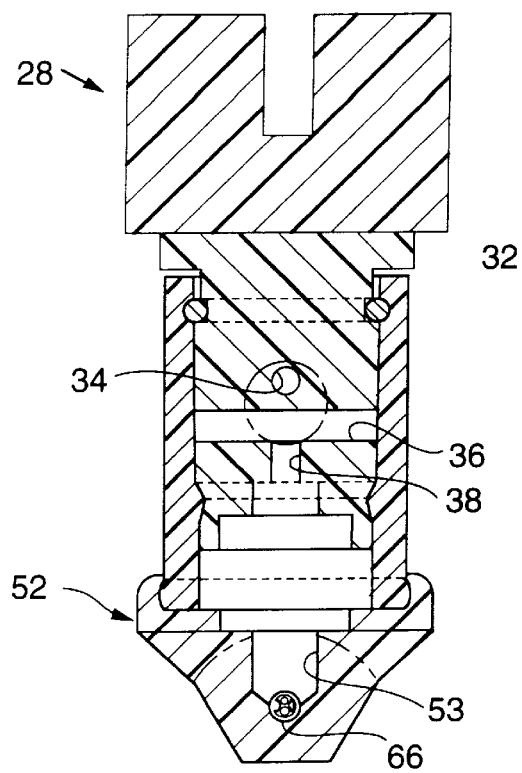
FIG. 5D is a cross section of the manifold in the opened position when coupled to a multiple lumen catheter.
Figure 5E:
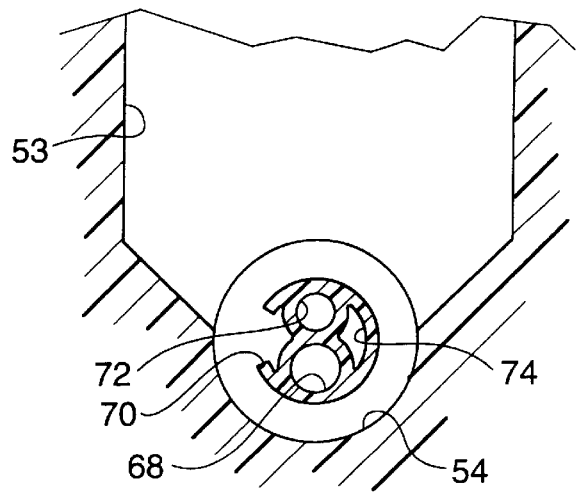
FIG. 5E is an enlarged view of the catheter shaft region of FIG. 5D.

FIG. 5D is a cross section of the manifold and catheter at the position indicated in FIG. 1B. FIG. 5E is an enlarged view of the catheter shaft region in FIG. 5D. Because valve gate 26 in the cross section is in the opened position, fluid communication exists between conduit 22 (not pictured) and vertical channel 38. Base channel 53 is contiguous with vertical channel 38 and provides a passageway to catheter shaft 66. At the junction where catheter shaft 66 and base channel 53 meet within elongated shaft 54, catheter shaft 66 includes an opening to the corresponding lumen 70. Catheter shaft 66 includes similar openings to lumens 72 and 74 at the corresponding junctions in the other bases 52.

Figure 6A:
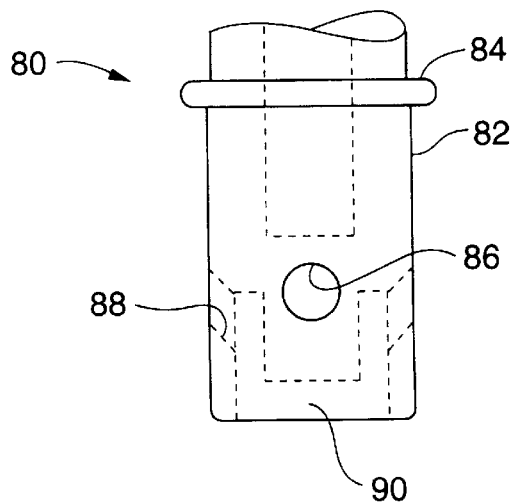
FIGS. 6A and 6B are front and side views of an alternative embodiment of the valve gate design for a second manifold embodiment.
Figure 6B:
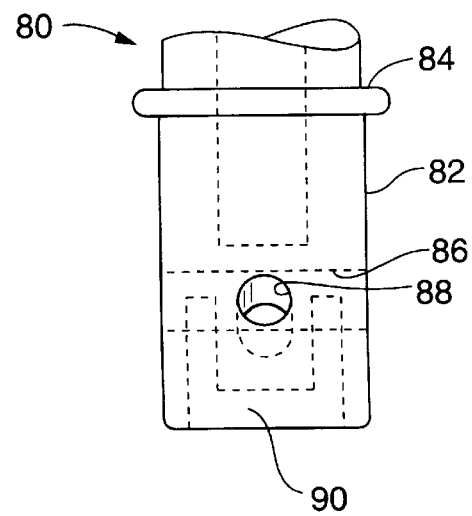

FIGS. 6A and 6B show a schematic for an alternate embodiment of the valve gates for use in a second manifold embodiment. The difference between this embodiment and the preferred valve gates depicted in FIGS. 1–5 is the orientation and design of the horizontal and vertical channels. All other aspects work of the manifold work are as previously described above and will not be repeated.

Referring to either FIG. 6A or 6B, alternate valve gate 80 comprises valve stem 82 which includes seal 84 and channels 86 and 88. As depicted by the side view of FIG. 6B, channel 86 forms a substantially straight passageway through valve stem 82 and is not linked to any other channel. In contrast, channel 88, from the opening on one side of valve stem 82, forms a downward passageway coupling vertical channel 90 and then continues to form an upward passageway to the opening out the other side of valve stem 82. The combination of channel 88 and vertical channel 90 forms a Y-shaped passageway.

When the alternative valve gate embodiment 80 is in the closed position, access is provided from the conduit (not pictured) through channel 86 to allow the other valve gates to be in fluid communication with the conduit via the entry port (not pictured). When valve gate 80 is in the opened position, channel 88 is in fluid communication with the conduit via the entry port. Because channel 88 is fluidly coupled to vertical channel 90, access is provided from the conduit via the entry port to the catheter lumen (not pictured) corresponding to valve gate 80. As illustrated by FIG. 6A, access is also simultaneously provided through channel 88 to allow other valve gates to be in fluid communication with the conduit via the entry port.

Figure 7:
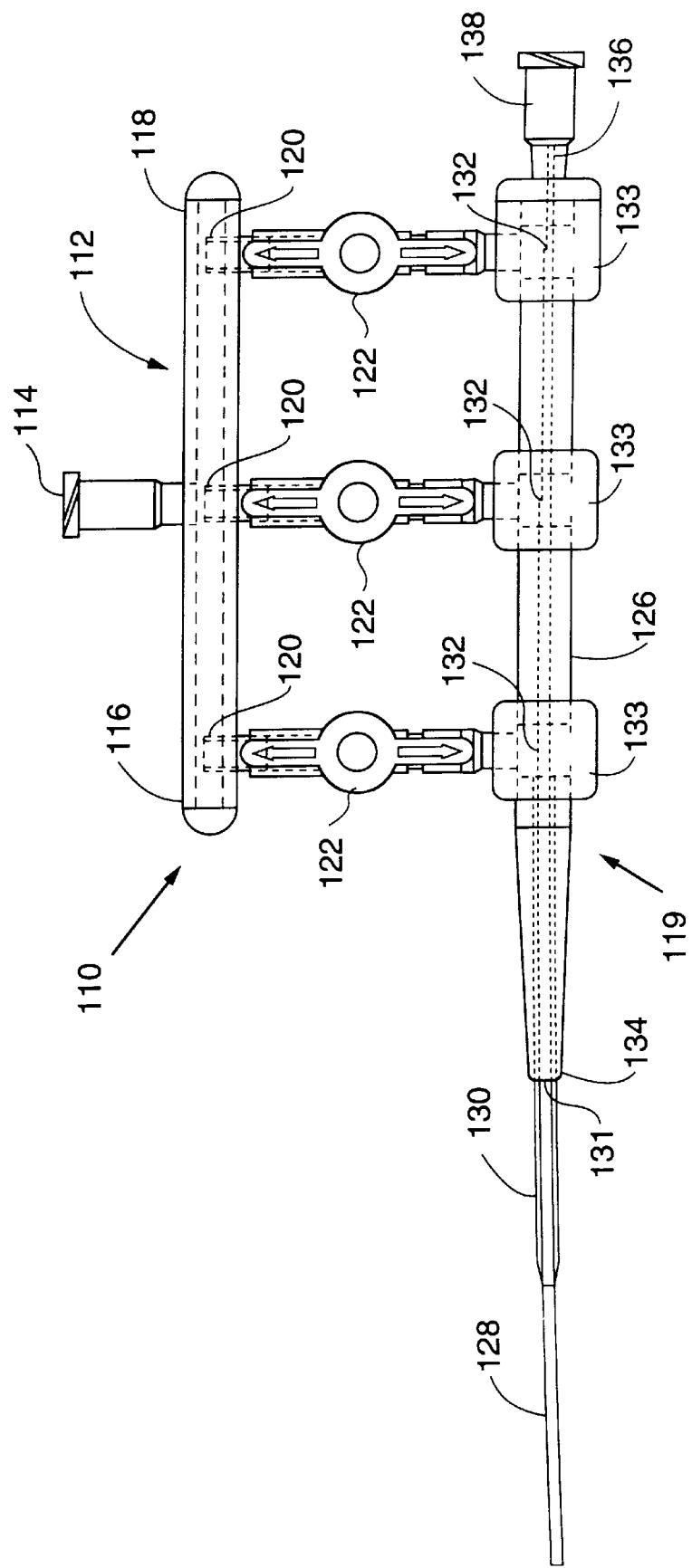
FIG. 7 shows a third embodiment of the inventive manifold.

FIG. 7 shows a third embodiment of the inventive catheter. The second embodiment comprises valve assembly 110 and attachment assembly 119. Valve assembly 110 comprises conduit 112, and a plurality of connectors 120, valve housings 121 (not seen in this view), and valve gates 122. Conduit 112 includes proximal end 118, distal end 116, and entry port 114. Although entry port 114 is pictured off to the side of conduit 112, entry port 114 may also be placed at either end of conduit 112. However, for ease of handling, placing the entry port 114 at the most proximal end 118 of conduit 112 is generally preferred.

Access from conduit 112 via entry port 114 to the three catheter lumens (not pictured) is controlled by valve gates 122 in the corresponding connectors 120. Although the three valves are used for the purposes of illustration, it is to be understood that the design may be readily adapted for use any number of valves (and thus catheter lumens) greater than or equal to two.

Each connector 120 fluidly couples conduit 112 to its corresponding catheter lumen and includes valve housing 121 and valve gate 122. Because a separate connector 120 is provided for each catheter lumen of interest, a less complicated design for valve gate 122 having only one horizonal channel 124 (not pictured) may be used. When valve gate 122 is placed in a closed position, no channel is provided through valve gate 122 to fluidly couple conduit 112 with its corresponding catheter lumen. When valve gate 122 is placed in an opened position, horizontal channel 124 provides access from conduit 122 via entry port 114 to its catheter lumen.

Attachment assembly 119 comprises elongated shaft 126 with distal end 134, proximal end 138, and access points 132 which links connector 120 and catheter shaft 128. Within each access point 132, catheter shaft 128 includes an opening to its corresponding catheter lumen. Access point 132 optionally may be reinforced by any reinforcement means 133 known in the art.

The most distal end 134 of elongated shaft 126 contains through-hole 131 for catheter shaft 128. Although a guide wire port 138 is shown at the most proximal end 136 of elongated shaft 126, depending on the nature of the catheter, the most proximal end 136 may alternatively be sealed. Additionally, a portion of catheter shaft 128 in the vicinity of through-hole 131 may be optionally sheathed by any suitable flexible material 130 to provide strain relief at this point.

Figure 8:
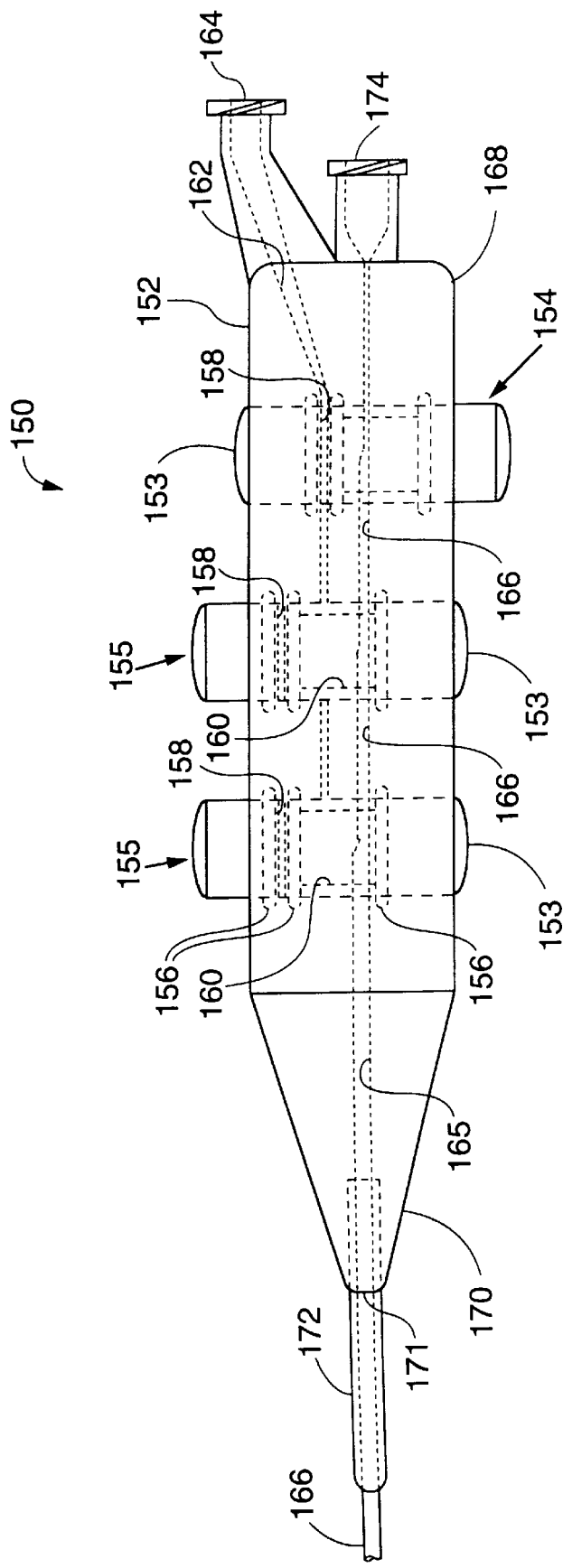
FIG. 8 shows a fourth embodiment of the manifold using an alternative mechanism for allowing fluid communication from a single port to the plurality of catheter lumens.

FIG. 8 shows a fourth embodiment of the inventive manifold using an alternative mechanism for allowing fluid communication from a single port to the plurality of catheter lumens. Although this manifold embodiment also controls access to three catheter lumens, it is to be understood that the design may be readily adapted for use with any number of catheter lumens greater or equal to two.

The inventive manifold 150 comprises (1) main body 152 which includes proximal end 168 and distal end 170, (2) plurality of push buttons 153, (3) conduit 162 with entry port 164, and (4) elongated shaft 165. Catheter shaft 166 is contained within elongated shaft 165. A through-hole 171 for catheter shaft 166 is provided at the most distal end 170 of main body 152. If desired, catheter shaft 166 may be reinforced with any suitable material along the portion of catheter shaft 166 in the immediate vicinity of through-hole 171. Depending on the nature of the catheter, elongated shaft 165 may extend from through-hole 171 through main body 152 and terminate at guide wire port 177 (as pictured) or may be sealed at a point within the proximal end 168 of main body 152 (not pictured).

As shown by FIG. 8, push buttons 153 includes three seals 156 which form upper chamber 158 and lower chamber 160 therein. As it will be further explained below, independent access to each catheter lumen from conduit 162 via entry port 164 is possible because either upper chamber 158 or lower chamber 160 of each push button 153 is in fluid communication with conduit 162. The geometric shape of push button 153 is unimportant. However, because standard "O" rings make suitable seals 156, cylindrical (or rod-like) push buttons 153 (as pictured) are generally preferred.

When push button 153 is in a closed position 154, upper chamber 158 that is formed by the upper two seals 156 is aligned with conduit 162. Upper chamber 158 functions only to continue conduit 162 to the next distal push button 153. When push buttons 153 are in an opened position 155, lower chamber 160 that is formed by the lower two seals 156 is aligned with conduit 162 so as to continue conduit 162 to the next distal push button 153. Lower chamber 160 is also fluidly coupled to elongated shaft 165 wherein catheter shaft 166 includes an opening to a catheter lumen. As a result, when push button 152 is in an opened position, access is provided to the corresponding catheter lumen from conduit 162 via entry port 164. Because each lower chamber 160 has access to a separate lumen within catheter shaft 166, independent access to each catheter lumen is possible from conduit 162.

It is to be understood that while the invention has been described above in conjunction with preferred embodiments, the description and examples are intended to illustrate and not limit the scope of the invention, which is defined by the scope of the appended claims.

What is claimed is:

1. A medical device, comprising:
    a catheter having a plurality of lumens and
    a manifold wherein the manifold includes
        a conduit having an entry port;
        a plurality of means for connecting the conduit to the plurality of catheter lumens, such that each catheter lumen is capable of being in fluid communication with the entry port;
        a plurality of means for controlling access from the conduit to the plurality of catheter lumens, such that each controlling means is capable of independently regulating access from the conduit to its corresponding catheter lumen.

2. The device as in claim 1 wherein the catheter includes a plurality of balloons mounted thereon.

3. A manifold for use with a multiple lumen catheter comprising:
    a conduit having an entry port;
    an elongated shaft for containing a catheter shaft therein; and,
    a plurality of valves disposed within the conduit,
    wherein at least two of the valves have an opened position and a closed position, and include a first channel and second channel formed therein, the first channel aligning with the conduit to provide access through the valve when the valved is placed in the closed position, and the second channel aligning with the conduit to provide access through the valve as well as to fluidly couple the conduit to the elongated shaft when the valve is placed in the opened position.

4. The manifold as in claim 3 wherein the number of valves is three.

5. The manifold as in claim 3 wherein the valve includes a handle and an elongated stem and the elongated stem includes the first channel and the second channel.

6. The manifold as in claim 5 wherein the first and second channels are in different axial planes within the stem, and the first channel is substantially linear and the second channel is a T-shaped passageway.

7. The manifold as in claim 5 wherein the first channel is substantially linear and the second channel is a Y-shaped passageway.

8. The manifold as in claim 6 wherein the valves are moved from the first position to the second position or vice versa by turning the handle by 90°.

9. The manifold as in claim 3 wherein the valves are cylindrical in shape, and are placed in the closed position or in the opened position by pushing the valves up or down.

10. A medical device comprising:
    a catheter having at least two lumens and
    a manifold wherein the manifold includes
        a conduit having an entry port;
        an elongated shaft for containing the catheter therein; and,
        a plurality of valves disposed within the conduit, wherein each valve corresponds to a catheter lumen, and wherein at least two of the valves have an opened position and a closed position, and include a first channel and second channel formed therein, the first channel aligning with the conduit to provide access through the valve when the valved is placed in the closed position, and the second channel aligning with the conduit to provide access through the valve as well as to fluidly couple the conduit to the elongated shaft when the valve is placed in the opened position.

11. The device as in claim 10 wherein the number of valves is three.

12. The device as in claim 10 wherein the valve includes a handle and a stem and the stem includes the first channel and the second channel.

13. The device as in claim 12 wherein the first and second channels are in different axial planes within the stem, and the first channel is substantially linear and the second channel is a T-shaped passageway.

14. The device as in claim 12 wherein the first channel is substantially linear and the second channel is a Y-shaped passageway.

15. The device as in claim 12 wherein the valves are moved from the first position to the second position or vice versa by turning the handle by 90°.

16. The device as in claim 10 wherein the valves are cylindrical in shape, and are placed in the closed position or in the opened position by pushing the valves up or down.

17. The device as in claim 10 wherein the catheter includes at least two balloons mounted thereon.

18. An apparatus for selectively coupling a single supply of fluid to separate first, second and third lumens of a catheter comprising:
    an intake conduit connectable to the fluid supply;
    an elongated shaft for containing a catheter shaft therein;
    a first valve located in the intake conduit and being movable between a closed and opened position, wherein in the closed position, fluid is permitted to pass through the first valve to the downstream side of the intake conduit but is prevented from entering the first lumen and wherein in the opened position, fluid is permitted to pass through the first valve to the downstream side of the intake conduit as well as entering the first lumen;
    a second valve located in the intake conduit downstream from the first valve and being movable between a closed and opened position, wherein in the closed position, fluid is permitted to pass through the second valve to the downstream side of the intake conduit but is prevented from entering the second lumen and wherein in the opened position, fluid is permitted to pass through the second valve to the downstream side of the intake conduit as well as entering the second lumen; and
    a third valve located in the intake conduit downstream from the third valve and being movable between a closed and opened position, wherein in the closed position, fluid is prevented from entering the third lumen and wherein in the opened position, fluid is permitted to enter the third lumen.

19. The apparatus as recited in claim 18 wherein each first and second valve including a first bore extending therethrough and providing fluid communication with the intake conduit when the valves are in the closed position and wherein each first and second valves further includes a second bore extending therethrough and providing fluid communication with the intake conduit and the associated lumen when the valve is in the opened position.

20. The apparatus as recited in claim 19 wherein the first and second valves are rotatable between the opened and closed positions.

21. The apparatus as recited in claim 20 wherein the first bore is linear.

22. The apparatus as recited in claim 21 wherein the second bore is T-shaped in configuration.

23. The apparatus as recited in claim 21 wherein the second bore is Y-shaped in configuration.

24. The apparatus as recited in claim 19 wherein the first and second valves are linearly translatable between the opened and closed positions.

25. The apparatus as recited in claim 24 wherein the first bore is a narrow linear bore and wherein the second bore has a width greater than the first bore so that the first bore overlaps with only the input conduit in the closed position, and the second bore overlaps with both input conduit and the associated lumen in the opened position.

* * * * *